(12) United States Patent
Govin et al.

(10) Patent No.: US 11,229,542 B2
(45) Date of Patent: Jan. 25, 2022

(54) APPARATUSES, SYSTEMS, AND METHODS FOR SOFT ROBOTIC BACK ORTHOSIS

(71) Applicants: ARIZONA BOARD OF REGENTS ON BEHALF OF ARIZONA STATE UNIVERSITY, Scottsdale, AZ (US); DIGNITY HEALTH, San Francisco, CA (US)

(72) Inventors: Deven Govin, Peoria, AZ (US); Laura Snyder, Scottsdale, AZ (US); Panagiotis Polygerinos, Gilbert, AZ (US); Grigoria Athanasaki, Tempe, AZ (US); Luis Saenz, Tolleson, AZ (US)

(73) Assignees: ARIZONA BOARD OF REGENTS ON BEHALF OF ARIZONA STATE UNIVERSITY, Scottsdale, AZ (US); DIGNITY HEALTH, San Francisco, CA (US)

( * ) Notice: Subject to any disclaimer, the term of this patent is extended or adjusted under 35 U.S.C. 154(b) by 352 days.

(21) Appl. No.: 16/276,064

(22) Filed: Feb. 14, 2019

(65) Prior Publication Data
US 2019/0247217 A1    Aug. 15, 2019

Related U.S. Application Data

(60) Provisional application No. 62/630,651, filed on Feb. 14, 2018.

(51) Int. Cl.
*A61F 5/02*    (2006.01)

(52) U.S. Cl.
CPC .............. *A61F 5/024* (2013.01); *A61F 5/022* (2013.01); *A61F 5/028* (2013.01)

(58) Field of Classification Search
CPC .......... A61F 5/028; A61F 5/024; A61F 5/026; A61F 5/03; A61F 13/14; A61F 5/05816;
(Continued)

(56) References Cited

U.S. PATENT DOCUMENTS

| 2,843,195 A | 1/1956 | Barvaeus |
|---|---|---|
| 5,256,135 A | 10/1993 | Avihod |

(Continued)

FOREIGN PATENT DOCUMENTS

WO    2019183397 A1    9/2019

OTHER PUBLICATIONS

Abbott et al., Early rehabilitation targeting cognition, behavior, and motor function after lumbar fusion: a randomized controlled trial. Spine (Phila Pa 1976) 2010;35(8):848-857.
(Continued)

*Primary Examiner* — Ophelia A Hawthorne
(74) *Attorney, Agent, or Firm* — Michael Best & Friedrich LLP

(57) ABSTRACT

A soft robotic spinal orthosis includes a control system having at least one processor, a plurality of adjustable pressure fluid bladders to provide at least one variable supporting force to a torso of a user, a plurality of supports to secure the fluid bladders to the torso, at least one sensor to detect a position of the torso, and at least one pressure device to increase and decrease a fluid pressure of the fluid bladders.

7 Claims, 12 Drawing Sheets

(58) Field of Classification Search
CPC . A61F 5/012; A61F 5/34; A61F 5/022; A61B 5/01
See application file for complete search history.

(56) References Cited

U.S. PATENT DOCUMENTS

| | | | |
|---|---|---|---|
| 5,362,304 | A | 11/1994 | Varn |
| 5,451,200 | A | 9/1995 | LaBella et al. |
| 5,950,628 | A * | 9/1999 | Dunfee ............ A61F 5/024 128/874 |
| 6,213,968 | B1 | 4/2001 | Heinz et al. |
| 6,840,916 | B2 | 1/2005 | Kozersky |
| 6,932,780 | B2 | 8/2005 | Kozersky |
| 7,001,348 | B2 | 2/2006 | Garth et al. |
| 7,150,048 | B2 * | 12/2006 | Buckman ............ A41D 13/018 2/465 |
| 7,316,660 | B1 | 6/2008 | Modglin |
| 7,819,831 | B2 * | 10/2010 | Dellanno ............ A47D 13/025 602/19 |
| 8,943,183 | B2 | 1/2015 | Prahlad et al. |
| 2001/0020144 | A1 | 9/2001 | Heinz et al. |
| 2005/0043660 | A1 * | 2/2005 | Stark ............ A61F 5/012 602/19 |
| 2008/0188785 | A1 | 8/2008 | Shutes et al. |
| 2014/0142485 | A1 * | 5/2014 | Berry ............ A61B 5/1116 602/19 |
| 2018/0289522 | A1 | 10/2018 | Zhu et al. |
| 2019/0029914 | A1 | 1/2019 | Polygerinos et al. |
| 2019/0167504 | A1 | 6/2019 | Polygerinos et al. |
| 2019/0314980 | A1 | 10/2019 | Polygerinos et al. |

OTHER PUBLICATIONS

Anderst et al., Six-Degrees-of-Freedom Cervical Spine Range of Motion During Dynamic Flexion-Extension After Single-Level Anterior Arthrodesis. J Bone Joint Surg Am. Mar. 20, 2013; 95(6): 497-506.
Aspen, "Evergreen 456 TLSO," <https://www.aspenmp.com/evergreentm-456-tlso.html> web page publicly available at least as early as Nov. 18, 2016.
Aspen, "Vista 637 LSO," <https://www.aspenmp.com/vista-lso.html> web page publicly available at least as early as Nov. 18, 2016.
Atlas et al. Long-term outcomes of surgical and nonsurgical management of lumbar spinal stenosis: 8 to 10 year results from the Maine Lumbar Spine Study. Spine. 2005;30(8):936-43.
Bergmark, Stability of the lumbar spine: a study in mechanical engineering. Acta Orthop Scand, 60 (Suppl 230) (1989), pp. 1-54.
Bydon et al., (2014). Lumbar fusion versus nonoperative management for treatment of discogenic low back pain. A systematic review and meta-analysis of randomized controlled trials. J Spinal Disord Tech; 27:297-304.
Cholewicki et al., Mechanical stability of the in vivo lumbar spine: implications for injury and chronic low back pain. Clinical Biomechanics vol. 11, No. 1. I-15, 1996.
Cholewicki et al., Lumbar spine load during the lifting of extremely heavy weights. Med Sci Sports Exerc, 23 (1991), pp. 1179-1186.
Christensen et al., Importance of the back-cafe concept to rehabilitation after lumbar spinal fusion: a randomized clinical study with a 2-year follow-up. Spine (Phila Pa 1976) 2003;28(23):2561-2569.
Crisco et al., Euler stability of the human ligamentous lumbar spine: Part II experiment. Clin Biomech, 7 (1992), pp. 27-32.
Delatorre, "TLSO Custom Back Brace," <https://www.delatorreop.com/tlso-custom-back-brace/> web page publicly available at least as early as Nov. 18, 2016.
Kalakoti et al. Inpatient outcomes and post-operative complications following primary versus revision lumbar spinal fusion surgeries for degenerative lumbar disc disease: a National (Nationwide) Inpatient Sample analysis 2002-2011. World Neurosurg. 2015:1-11.
Koenders et al., Pain and disability following first-time lumbar fusion surgery for degenerative disorders: a systematic review protocol. Systematic Reviews (2016) 5:72.
McGill et al., Partitioning of the L4-5 dynamic moment into disc, ligamentous and muscular components during lifting. Spine, 11 (1986), pp. 666-678.
Nielsen et al., Costs and quality of life for prehabilitation and early rehabilitation after surgery of the lumbar spine. BMC Health Serv Res. 2008;8:209. doi: 10.1186/1472-6963-8-209.
Nielsen et al., Prehabilitation and early rehabilitation after spinal surgery: randomized clinical trial. Clin Rehabil. 2010;24(2):137-148.
Ong et al. Perioperative outcomes, complications, and costs associated with lumbar spinal fusion in older patients with spinal stenosis and spondylolisthesis. Neurosurg Focus. 2014;36(6):E5.
Puffer et al., Patient-specific factors affecting hospital costs in lumbar spine surgery. Journal of Neurosurgery: Spine, Jan. 2016 / vol. 24 / No. 1 : pp. 1-6.
Rajaee et al. Spinal fusion in the United States: analysis of trends from 1998 to 2008. Spine (Phila Pa 1976). 2012;37 (1):67-76.
Virk et al., Cost effectiveness analysis of graft options in spinal fusion surgery using a Markov model. J Spinal Disord Tech. 2012;25(7):E204-10.
Albert et al., Modic changes, possible causes and relation to low back pain, All The Back Research Center, Part of Clinical Locomotion Science, University of Southern Denmark, Lindevej 5, 5750 Ringe, Denmark. Med Hypotheses. 2008;70(2):361-8.
Farrar et al., Acne: inflammation, Clinics Dermatol, 22 (2004), pp. 380-384.
Van Tulder et al., Low back pain. Best Pract Res Clin Rheumatol., 2002, 16(5):761-775.
"Erector Spinae." John The Bodyman Fitness Academy, Press, May 28, 2014, www.johnthebodyman.com/back-muscles/back-muscles/.
U.S. Appl. No. 15/829,597.
U.S. Appl. No. 16/396,409.
U.S. Appl. No. 16/486,072.

* cited by examiner

APPARATUSES, SYSTEMS, AND METHODS FOR SOFT ROBOTIC BACK ORTHOSIS

CROSS-REFERENCE TO RELATED APPLICATION

This application claims the benefit of U.S. Provisional Patent Application No. 62/630,651, filed Feb. 14, 2018, the entire contents of which are incorporated by reference herein.

FIELD OF THE INVENTION

This disclosure relates generally to methods, apparatuses, and systems for soft robotic back orthosis. An object of the embodiments of this disclosure is to relieve back pain by limiting patient motion from the fully upright position and to stabilize the lumbosacral spine.

BACKGROUND

Lumbar Spinal Fusion (LSF) is a surgery designed for decompression and stabilization of the lumbar spine to treat numerous spinal disorders including disc herniation, spinal stenosis, spondylolisthesis, and discogenic low back pain. A recent analysis of trends in spinal fusion procedures in the U.S. has shown a significant increase in hospitalization and national medical bills. However, the reason for this increase is unclear, since the results from relative studies have been inconclusive, with no further understanding of long-term outcomes after the surgery.

The lumbar spine consists of five lumbar vertebrae between the thoracic spine and the sacrum. Its function is to protect and support the spinal cord and spinal nerves during the performance of daily activities. The lumbar part of the spine buckles under compressive loads over approximately 90 N; although, in vivo, it can tolerate loads in the range of 6000-18000 N during more demanding activities. The conditions of mechanical stability and torque of the human lumbar spine have been well documented. Six degrees of freedom describe the spinal motion: 3 translational degrees and 3 rotational degrees.

Some of the major injuries that occur in the spine are vertebral compression fractures and lumbar spondylosis. Vertebral compressions tend to require surgery immediately, and require a spinal orthosis post-operation to help support the spine. Lumbar spondylosis is important to address immediately because it can result to lumbar spondylolisthesis, which is a worsened condition that will require surgery. A spinal orthosis is one of the major methods used to prevent lumbar spondylosis from worsening. The effectiveness of rehabilitation after LSF surgery vanes, depending on the timing of intervention and exercise protocols, according to recent studies. A new spinal orthotic device is needed to provide both desired flexibility and support during the rehabilitation process.

SUMMARY

The orthotic device according to embodiments of the present disclosure was created to help patients who have undergone a spinal surgery and will need to wear a brace to help stabilize their spinal column. Usually patients are given a back brace that will limit their motion by using hard plates. However, these often get uncomfortable after prolonged use. The proposed device can utilize fluid bladders to create a variability in stiffness based on a position of the back. This variability may create a more comfortable brace for long term use. In some embodiments, the fluid bladders are air bladders.

In some embodiments, a soft robotic spinal orthosis includes a control system having at least one processor, a plurality of adjustable pressure fluid bladders to provide at least one variable supporting force to a torso of a user, a plurality of supports to secure the fluid bladders to the torso, at least one measuring device (i.e., sensor) to detect a position of the torso, and at least one pressure device to increase and decrease a fluid pressure of the fluid bladders.

In some embodiments, the control system receives a torso position from the measuring device and determines a magnitude of the variable supporting force sufficient to support the torso based on the torso position. The control system enables the pressure device to modify a pressure of the fluid bladders to supply the variable supporting force to the torso at the determined magnitude.

In some embodiments, the control system is programmable and controls one or more variable supporting force magnitudes and one or more variable supporting force application time intervals. In some embodiments, at least one fluid bladder supports a front of a waist of the user, at least one fluid bladder supports a back of the waist, and a plurality of fluid bladders extending along a spine of the torso support the spine. In some embodiments, the measuring device is an inertial measurement unit (IMU).

In some embodiments, the pressure device includes at least one pump to provide fluid pressure, at least one manifold having at least one valve to receive the fluid pressure from the pump, and at least one pressure sensor to determine a fluid pressure inside the fluid bladders and control an inflow and outflow of fluid pressure to the fluid bladders. In some embodiments, the fluid bladders that support the waist stabilize the torso and the fluid bladders extending along the spine limit one or more of flexion and extension motions of the spine. In some embodiments, the fluid bladders that support the waist are arranged in a cascading configuration along a height of the waist.

In at least one embodiment, a soft robotic spinal orthosis apparatus includes a first fluid bladder to provide at least one variable supporting force to a waist of a user, and a second fluid bladder to provide at least one variable supporting force to a back of the user. A first support secures the first fluid bladder to the waist, and a second support secures the second fluid bladder to the back. A measuring device detects a position of the waist or the back. A pressure device adjusts a fluid pressure in the first fluid bladder and in the second fluid bladder based on the position detected by the measuring device.

In yet another embodiment, a soft robotic spinal orthosis apparatus includes a first fluid bladder to provide at least one variable supporting force to a front of a waist of a user, a second fluid bladder to provide at least one variable supporting force to a back of the user, and a third fluid bladder to provide at least one variable supporting force to a back of the waist of a user. A first support secures the first fluid bladder and the third fluid bladder to the waist. A second support secures the second fluid bladder to the back. A measuring device detects a position of the waist or the back. A control system includes at least one processor. The control system is in communication with the measuring device and the processor receives a signal corresponding to the position detected by the measuring device. A pressure device adjusts a fluid pressure in the first fluid bladder, in the second fluid bladder, and in the third fluid bladder based on a signal from the processor.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

In general, the present subject matter relates to a back orthosis including a soft robotic apparatus. The orthosis may assist in supporting a user's torso (e.g., a user's waist, a user's back, or a user's spine). Embodiments of the disclosed soft robotic back orthosis device utilize soft robotics to create a back orthosis that can adjust the amount of support the device provides through changing its stiffness.

FIGS. 1-4 illustrate an orthosis device, generally designated 10. FIGS. 5-9 illustrate an orthosis device 110 according to another embodiment. At least some difference and similarities are described below. Similar features are identified by similar reference numbers, where possible.

Figure 1:
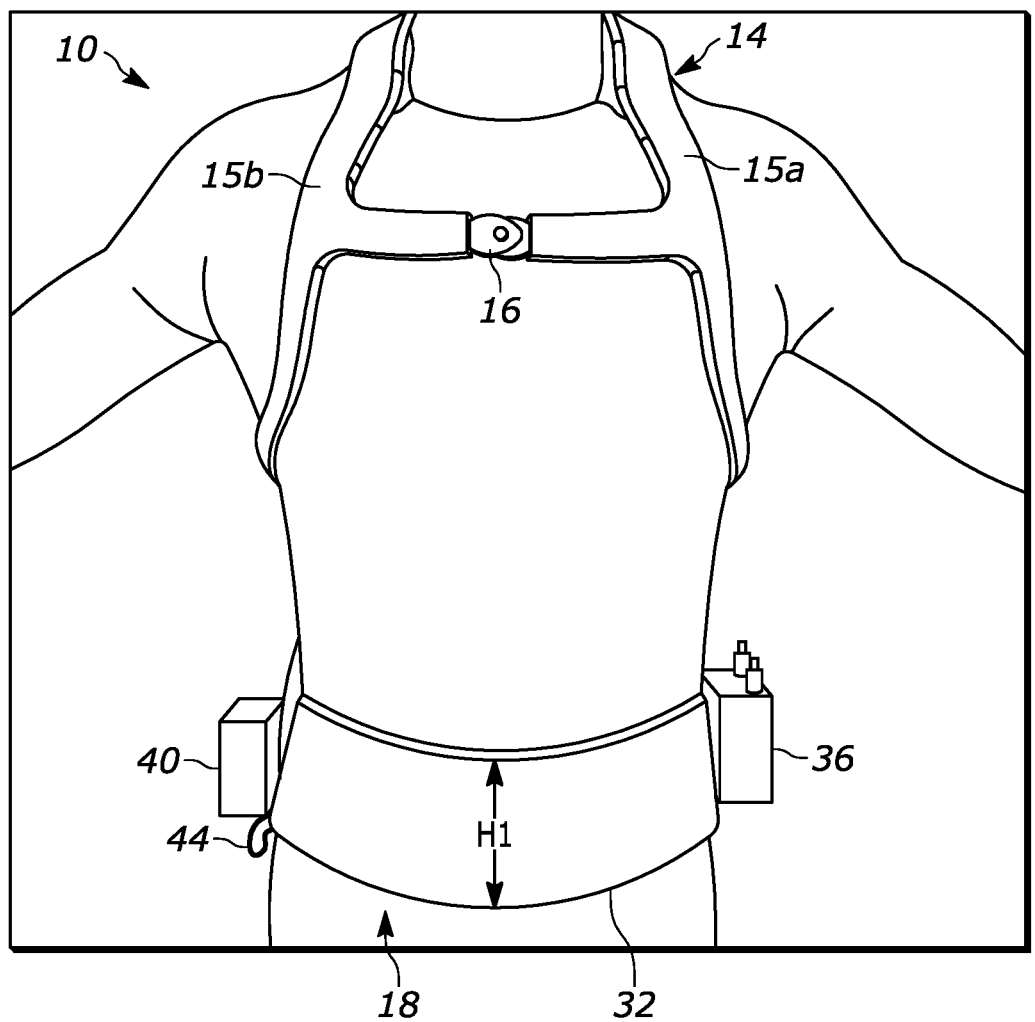
FIG. 1 is a front view of an orthosis device in accordance with one embodiment, worn by a user.
Figure 2:
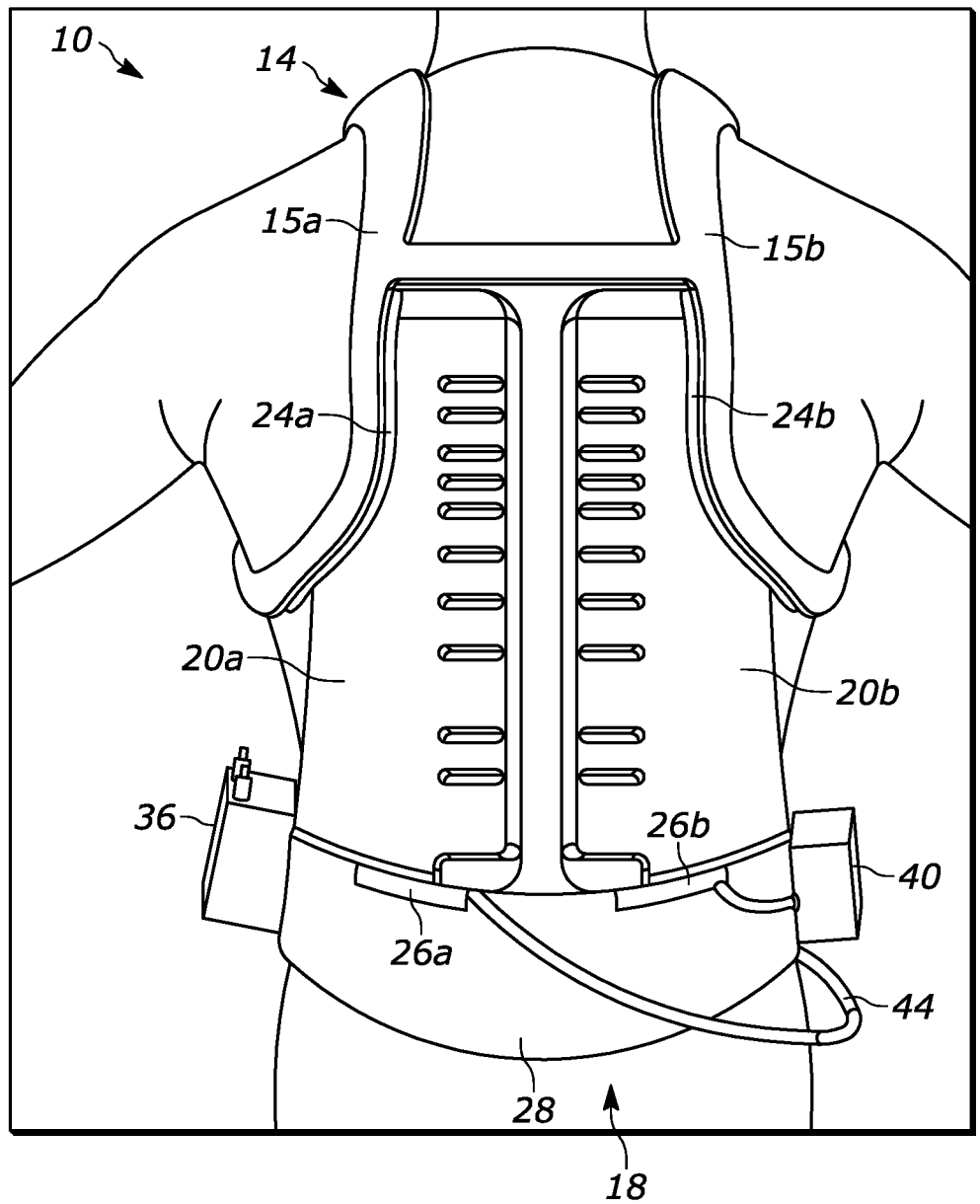
FIG. 2 is a rear view of the orthosis device of FIG. 1.

As shown in FIGS. 1 and 2, the orthosis device 10 includes a first support or harness 14. In the illustrated embodiment, the harness 14 is a backpack harness, and is worn over a user's shoulders. The harness 14 includes a first or left shoulder strap 15a and a second or right shoulder strap 15b. The straps 15a, 15b may be releasably coupled together with a connector 16 (see e.g., FIG. 1). A coupled position of the connector 16 secures the harness 14 to the user, while in an uncoupled position, the user may remove the harness 14. In the illustrated embodiment, the connector 16 is a buckle. In other embodiments, the connector 16 may be Velcro, a clip, any other suitable connector.

The orthosis device 10 also includes a second support or waist belt 18, which is supported on the user's body, proximate the hips. The waist belt 18 has a height $H_1$ that is configured to substantially cover the user's waist. In the illustrated embodiment, the waist belt 18 wraps entirely around a user's waist and is secured by Velcro, a buckle, a clip, or other suitable connector. In some embodiments, the waist belt 18 and the harness 14 are separate (e.g., one can be worn without the other), while in other embodiments the harness 14 and the waist belt 18 are coupled together (e.g., both must be worn at the same time).

With reference to FIG. 2, the orthosis device 10 further includes a first or left encapsulated fluid bladder 20a and a second or right encapsulated fluid bladder 20b. In some embodiments, the encapsulated fluid bladders 20a, 20b are air bladders, but other suitable gases or fluids may be used to inflate the fluid bladders 20a, 20b. The fluid bladders 20a, 20b are supported on the user's back by the harness 14 and the waist belt 18. In the illustrated embodiment, the harness 14 includes a left attachment point 24a and a right attachment point 24b. The waist belt 18 also includes a left attachment point 26a and a right attachment point 26b. The left fluid bladder 20a is coupled between the left attachment point 24a or the harness 14 and the left attachment point 26a of the waist belt 18. The right fluid bladder 20b is coupled between the right attachment point 24b or the harness 14 and the right attachment point 26b of the waist belt 18. In some embodiments, the attachment points 24a, 24b, 26a, 26b may be snaps, Velcro, clips, or any other suitable connector.

In some embodiments, the waist belt 18 includes additional fluid bladders. In the illustrated embodiment, the waist belt 18 includes a rear fluid bladder 28 and a front fluid bladder 32 (see e.g., FIG. 1). The fluid bladders 28, 32 wrap at least partially around the user's body (e.g., the rear fluid bladder 28 is disposed proximate the user's lower back and the front fluid bladder 32 is disposed below the user's chest). In other embodiments, the fluid bladders 28, 32 may be a single fluid bladder that wraps entirely around the user's waist. In still other embodiments, the waist belt 18 may include only a rear fluid bladder 28 or a front fluid bladder 32.

Figure 3:
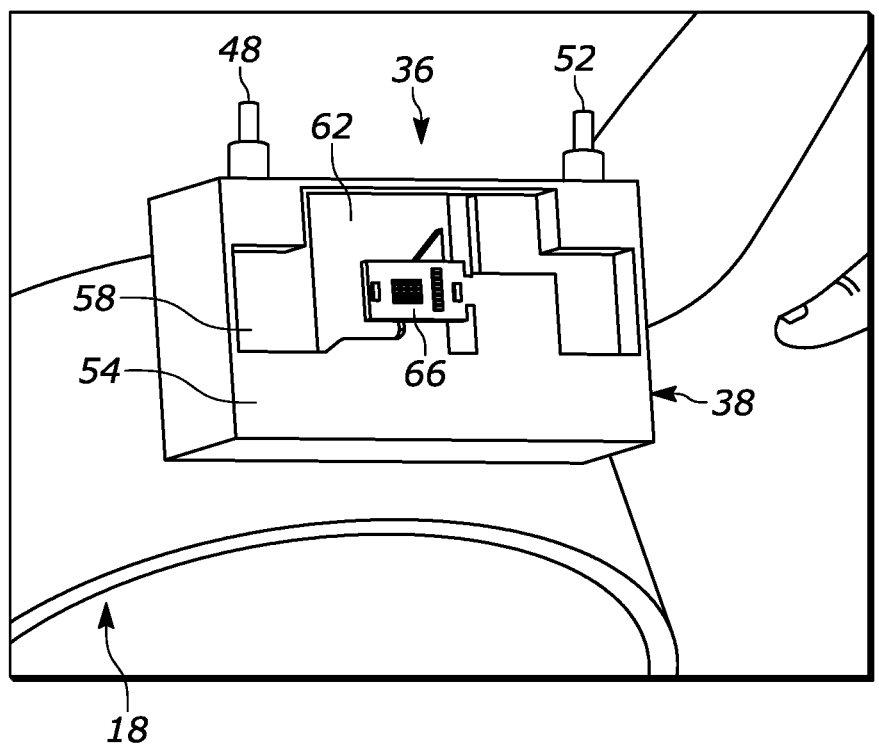
FIG. 3 is a perspective view of a control box used with the orthosis device of FIG. 1.

As shown in FIG. 3, a measuring or control device 36 is coupled to the waist belt 18. The control device 36 is shown on the user's left (see e.g., FIG. 2), although the control box 36 may be repositionable to the user's right, or may be positioned at other locations. The control device 36 includes a housing 38, which may include a clip (not shown) to couple to the waist belt 18. A first or power switch 48 and a second or emergency off switch 52 extend from the housing 38. A battery 54, a power regulator 58, a MOSFET transistor 62, and a processor or microcontroller 66 (e.g., an Arduino) are supported within the housing 38. The microcontroller 66 is in electrical communication with the MOSFET transistor 62 and the battery 54. The power switch 48 and the emergency off switch 52 are each in electrical communication with the battery 54, the power regulator 58, and the microcontroller 66 in order to selectively supply electrical current to the microcontroller 66.

Figure 4:
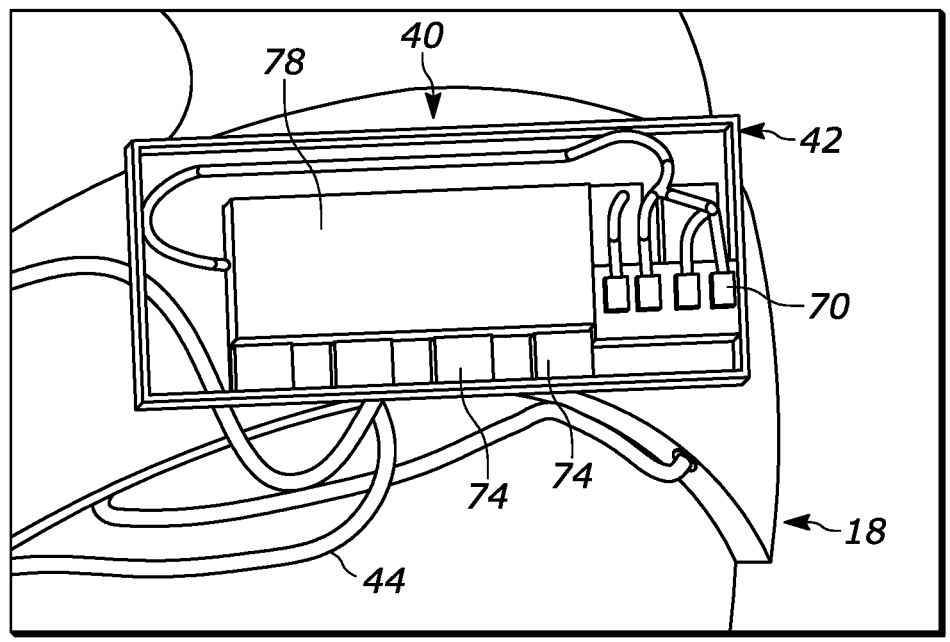
FIG. 4 is a perspective view of a pneumatic box used with the orthosis device of FIG. 1.

As shown in FIG. 4, a pressure or pneumatic device 40 is coupled to the waist belt 18. The pneumatic device 40 is shown on the user's right (see e.g., FIG. 2), although the pneumatic device 40 may be repositionable to the user's left, or may be positioned at other locations. The pneumatic device 40 includes a housing 42, which may include a clip (not shown) to couple to the waist belt 18. Pumps 70, pressure sensors 74, and a manifold housing 78 are supported within the housing 42. The manifold housing 78 supports at least one manifold and includes at least one valve (e.g., a solenoid valve—neither shown). The valve is configured to receive the fluid pressure from the pumps 70. The pressure sensors 74 are in fluid communication with both the manifolds in the manifold housing 78 and the fluid bladders 120a, 120b, 128, 132. Tubing 44 is connected to the manifold housing 78, and extends from the housing 42. The tubing 44 provides fluid communication between the pumps 70 and the fluid bladders 20a, 20b, 28, 32.

Figure 5:
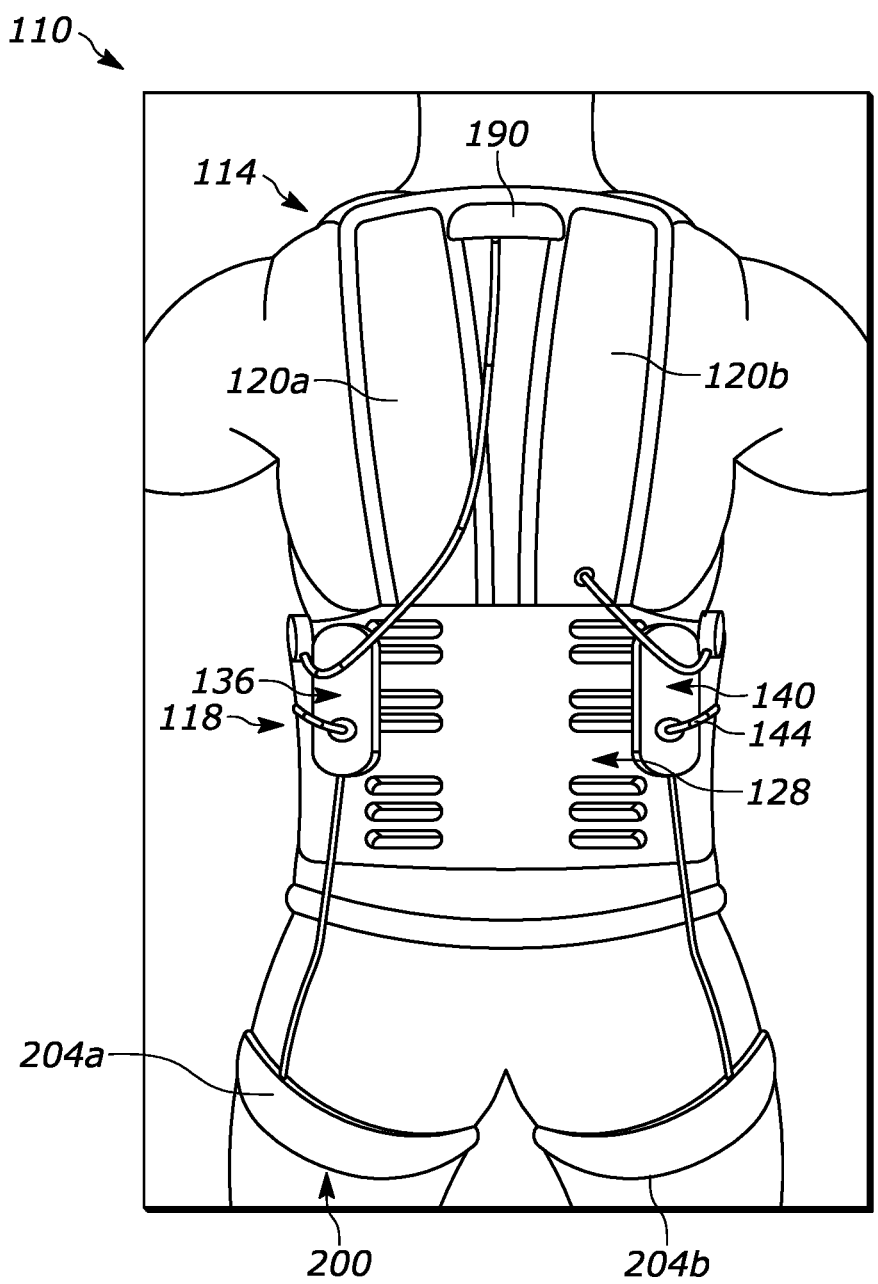
FIG. 5 is a rear view of an orthosis device according to another embodiment, worn by a user.
Figure 6:
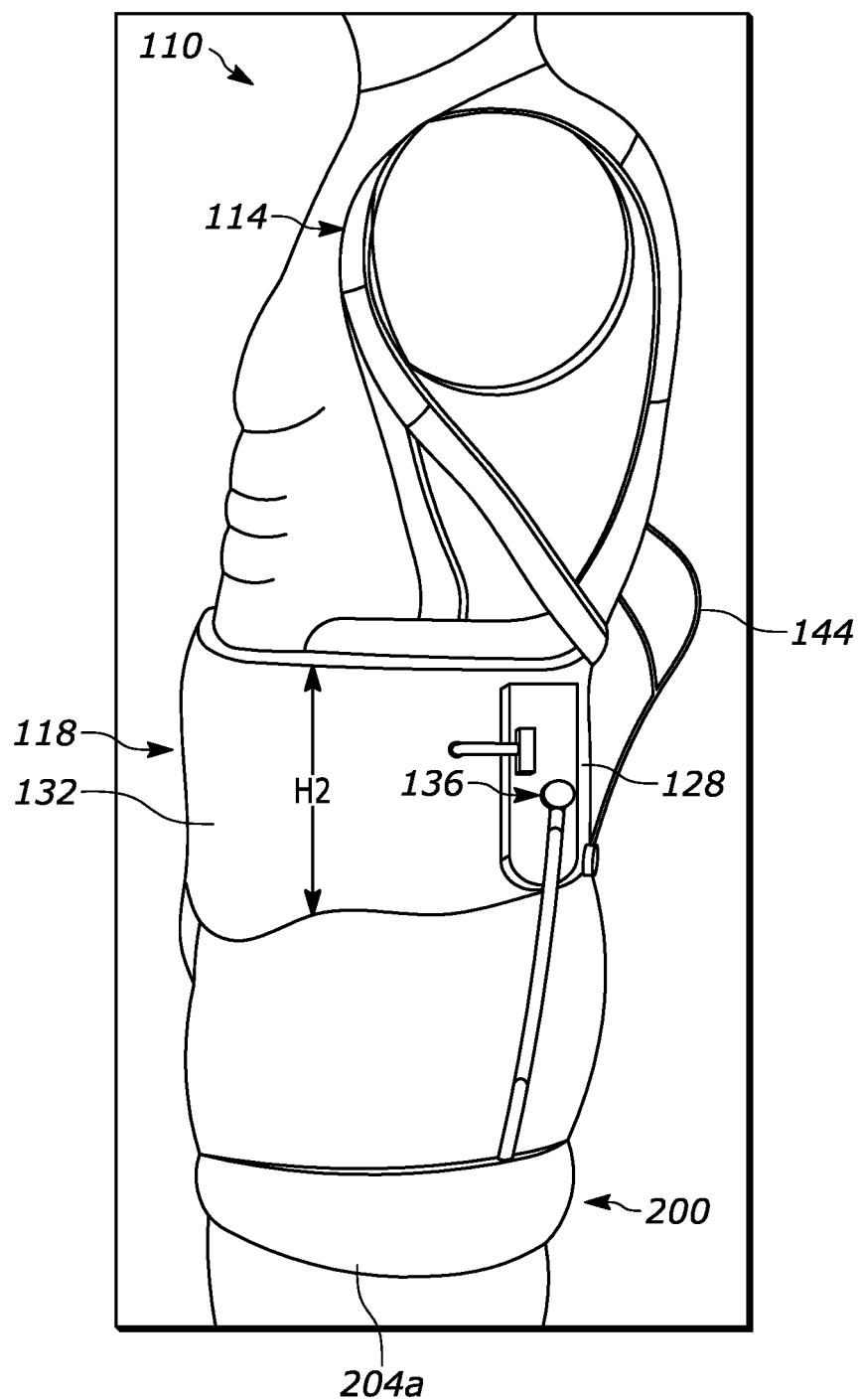
FIG. 6 is a side view of the orthosis device of FIG. 5.

Referring now to FIGS. 5 and 6, another embodiment of an orthosis device 110 is shown. In the illustrated embodiment, the orthosis device 110 includes a first support or shoulder harness 114, a second support or waist belt 118, and a third support or leg harness 200.

Figure 7:
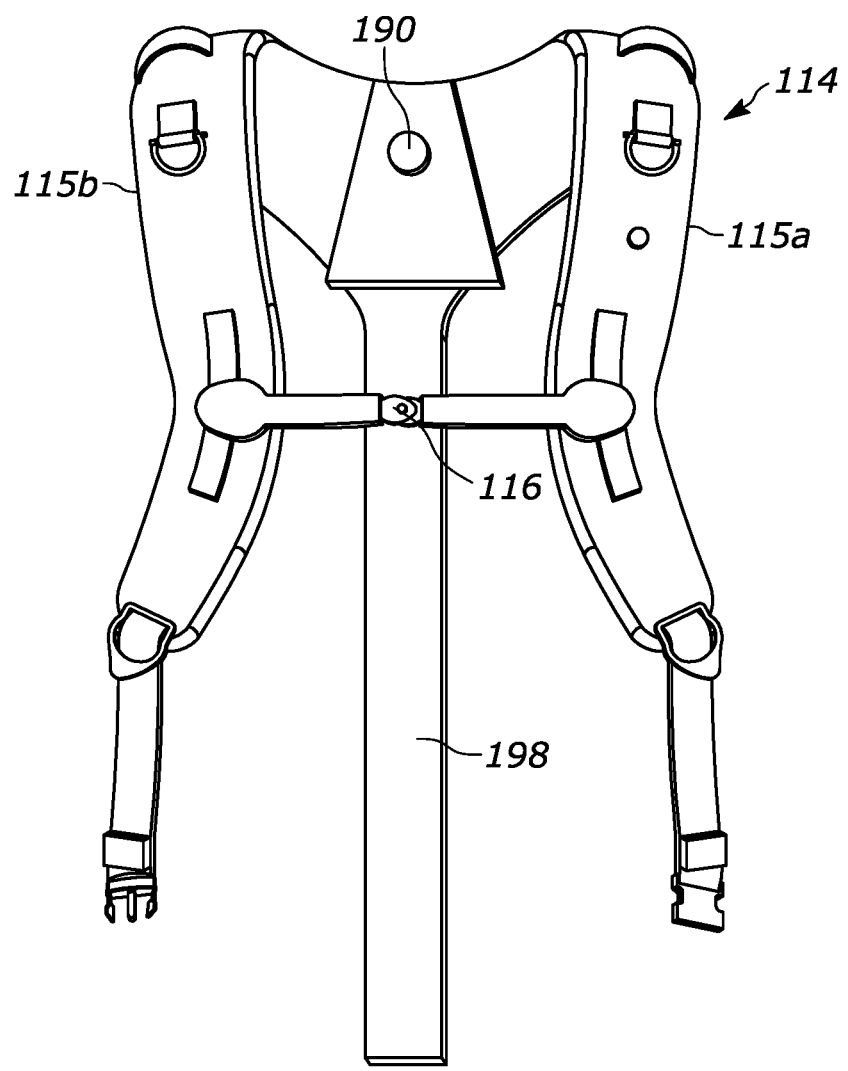
FIG. 7 is a front view of a first harness used with the orthosis device of FIG. 5.

Referring now to FIG. 7, the shoulder harness 114 includes a left shoulder strap 115a and a right shoulder strap 115b. A connector 116 is partially formed on both shoulder straps 115a, 115b, and is releasably coupled together to secure the shoulder straps 115a, 115b on the user. In the illustrated embodiment, the connector 116 is a buckle. In other embodiments, the connector 116 may be Velcro, a clip, any other suitable connector. The shoulder harness 114 may also include a rigid support 198 that extends at least partially along the length of the spine. The rigid support 198 rests against the spine and may be metal, plastic, or a similar rigid material. In the illustrated embodiment, the rigid support 198 has a rectangular cross-section, although in other embodiments, the rigid support 198 may have a circular cross-section (e.g., a rod), or other similar cross-sections (e.g., triangular). In some embodiments, the orthosis device 110 contains no rigid support 198, meaning it conforms to the body better than a traditional brace.

Figure 8:
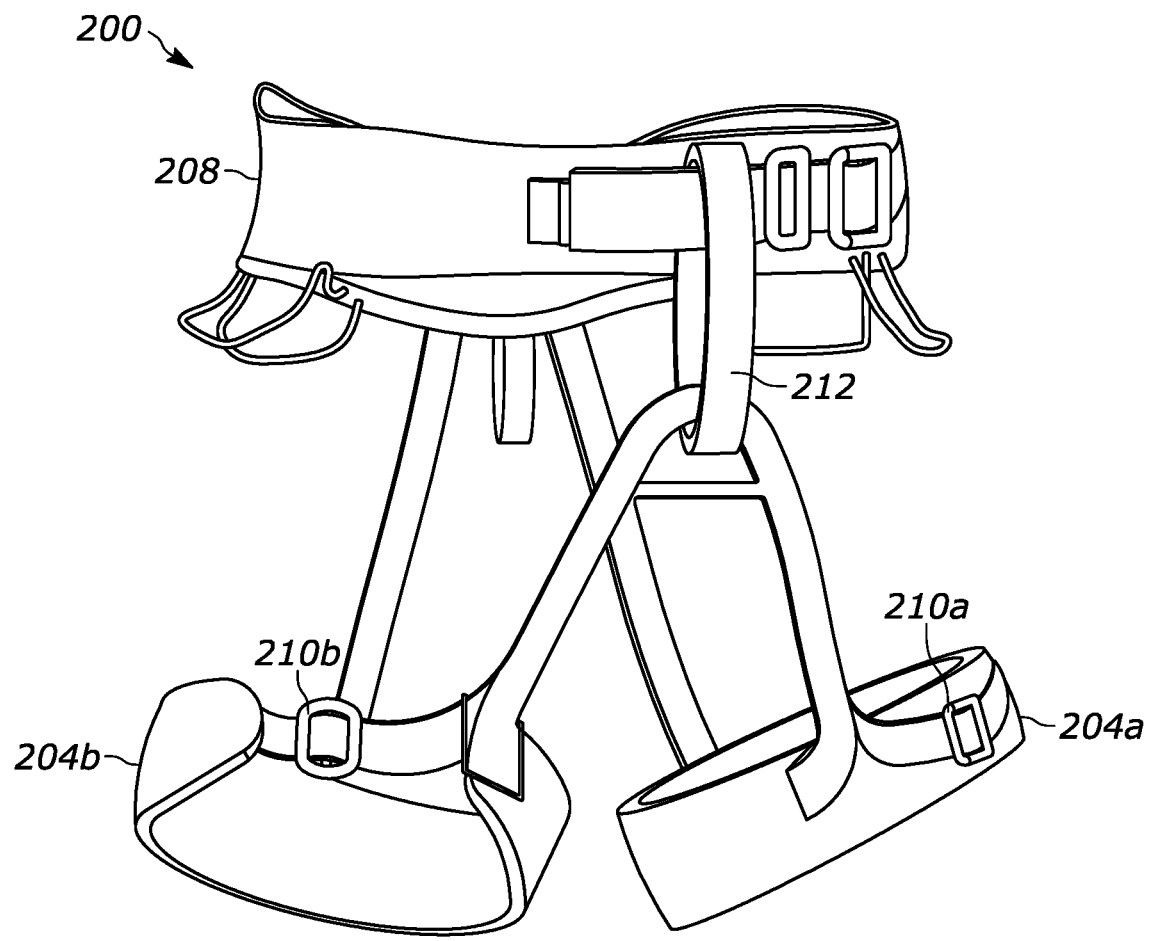
FIG. 8 is a perspective view of a second harness used with the orthosis device of FIG. 5.
Figure 9:
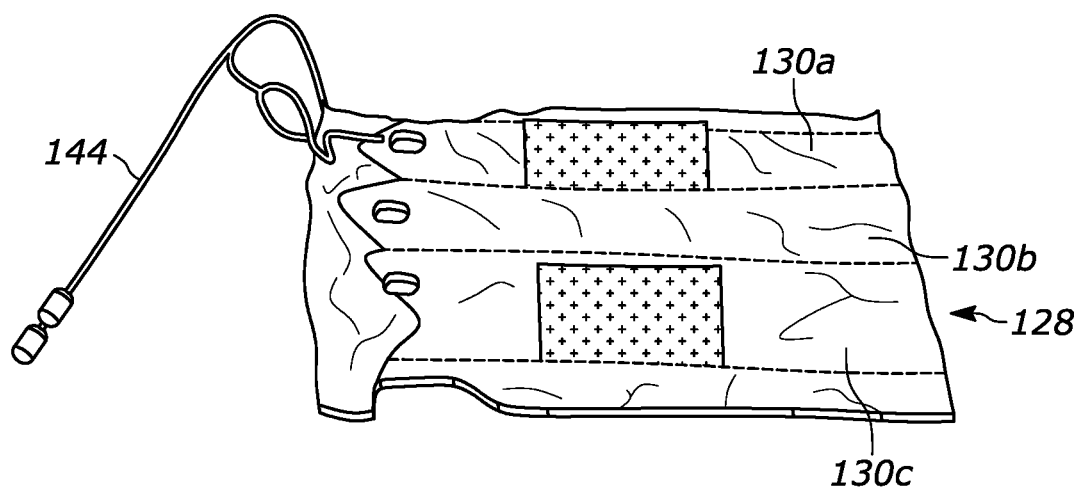
FIG. 9 is a perspective view of a first fluid bladder used with the orthosis device of FIG. 5.

Referring now to FIG. 8, the leg harness 200 includes a left leg attachment 204a, a right leg attachment 204b, and a belt 208. In use, the left leg attachment 204a is secured to the upper thigh of the left leg, and the right leg attachment 204b is secured to the upper thigh of the right leg. Each leg attachment 204a, 204b may include an adjustment mechanism 210a, 210b to tighten or loosen each leg attachment 204a, 204b relative to the respective leg (e.g., right or left). In the illustrated embodiment, the adjustment mechanisms 210a, 210b are slide buckles that allows a piece of material (e.g., fabric) to be tightened to loosened.

Each leg attachment 204a, 204b is coupled to the belt 208, which is supported around the user's waist. In the illustrated embodiment, the leg attachments 204a, 204b are supported on a front of the belt 208 by a support loop 212, and are attached directly to a back of the belt 208. The support loop 212 provides the user with freedom of movement (i.e., the leg attachments 204a, 204b have a wide range of motion relative to the belt 208), while still supporting the leg attachments 204a, 204b. The belt 208 may include Velcro, or other suitable fastener, in order to couple to the user's waist.

With continued reference to FIGS. 5 and 6, the orthosis device 110 includes a left and right fluid bladder 120a, 120b, respectively, coupled to the back harness 114. The orthosis device 110 also includes a back and front fluid bladder 128, 132, respectively, coupled to the waist belt 118. A control device 136 and a pneumatic device 140 are coupled to the waist belt 118, and tubing from the pneumatic device 140 provides fluid communication to the fluid bladders 120a, 120b, 128, 132. The internal components of the control device 136 and the pneumatic device are substantially identical to the control device 36 and the pneumatic device 40 described above.

Figure 10:
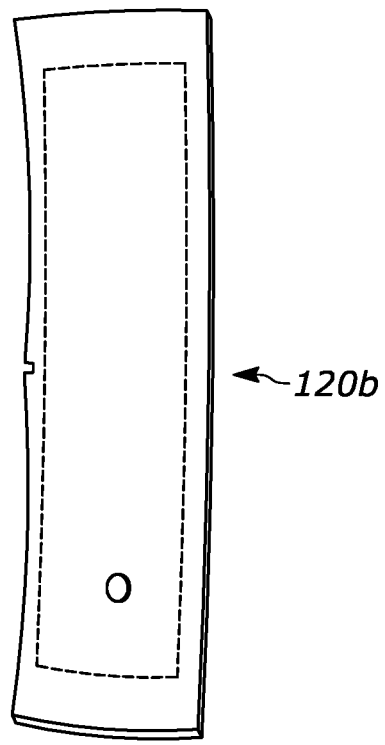
FIG. 10 is a front view of a second fluid bladder used with the orthosis device of FIG. 5.
Figure 11B:
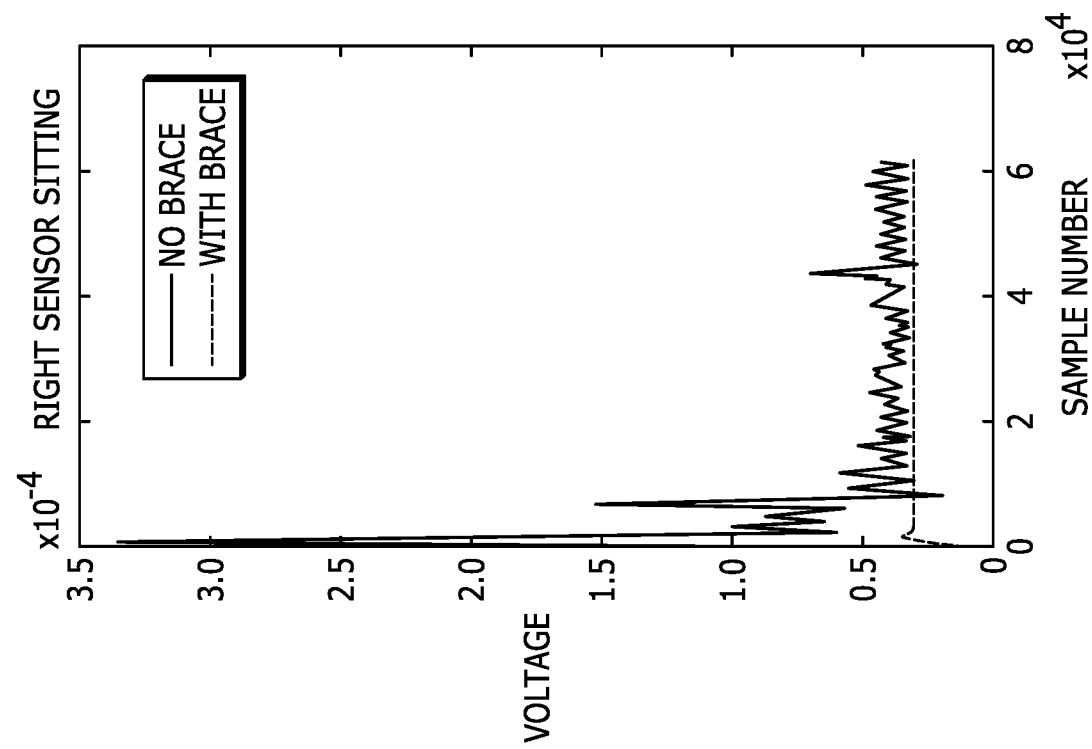
FIG. 11B is a graph comparing voltage readings from a second sensor while a user is sitting with and without the orthosis device of FIG. 1.
Figure 11A:
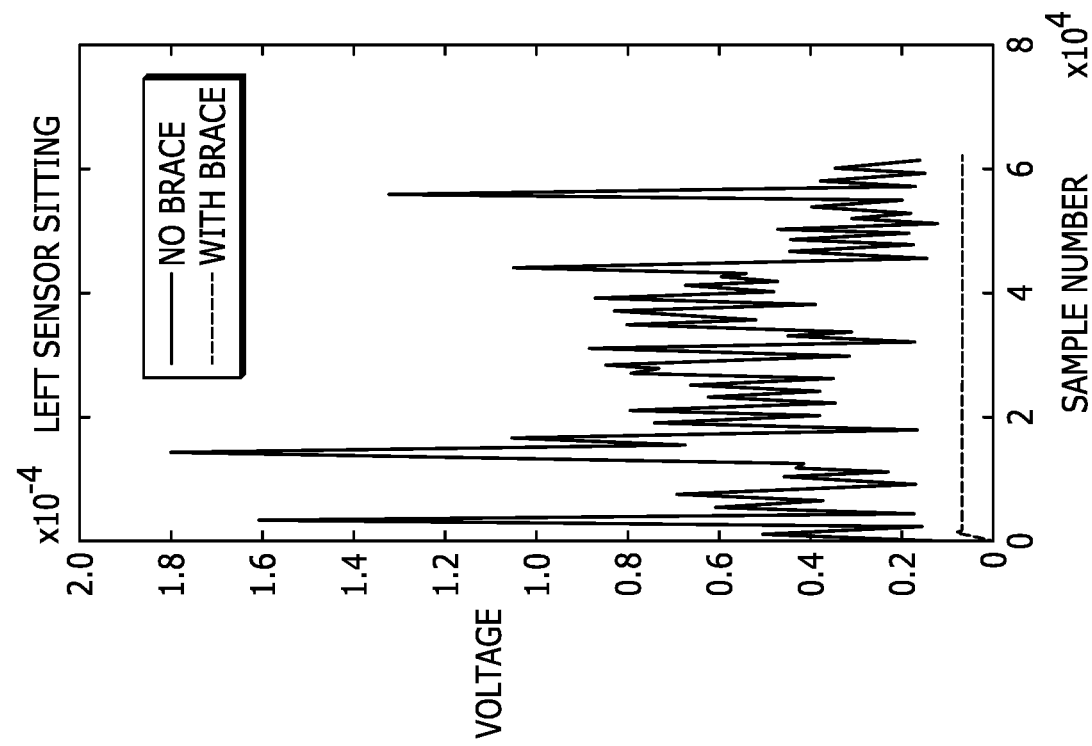
FIG. 11A is a graph comparing voltage readings from a first sensor while a user is sitting with and without the orthosis device of FIG. 1.
Figure 12B:
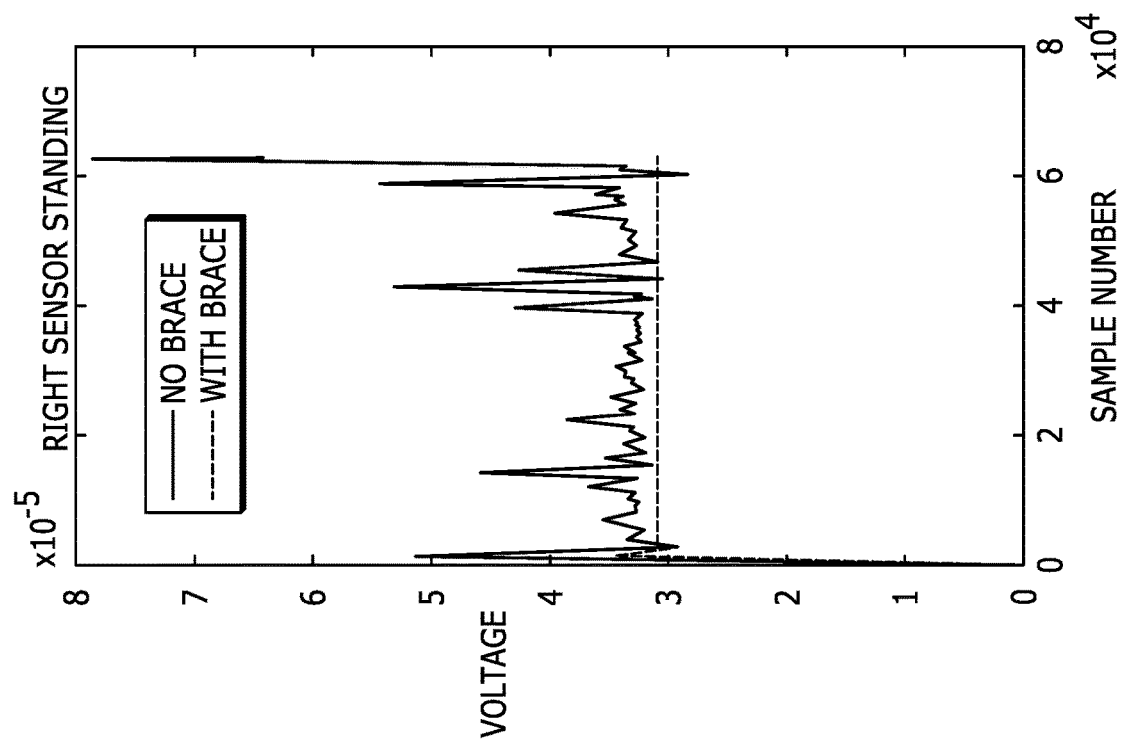
FIG. 12B is a graph comparing voltage readings from the second sensor while a user is standing with and without the orthosis device of FIG. 1.
Figure 12A:
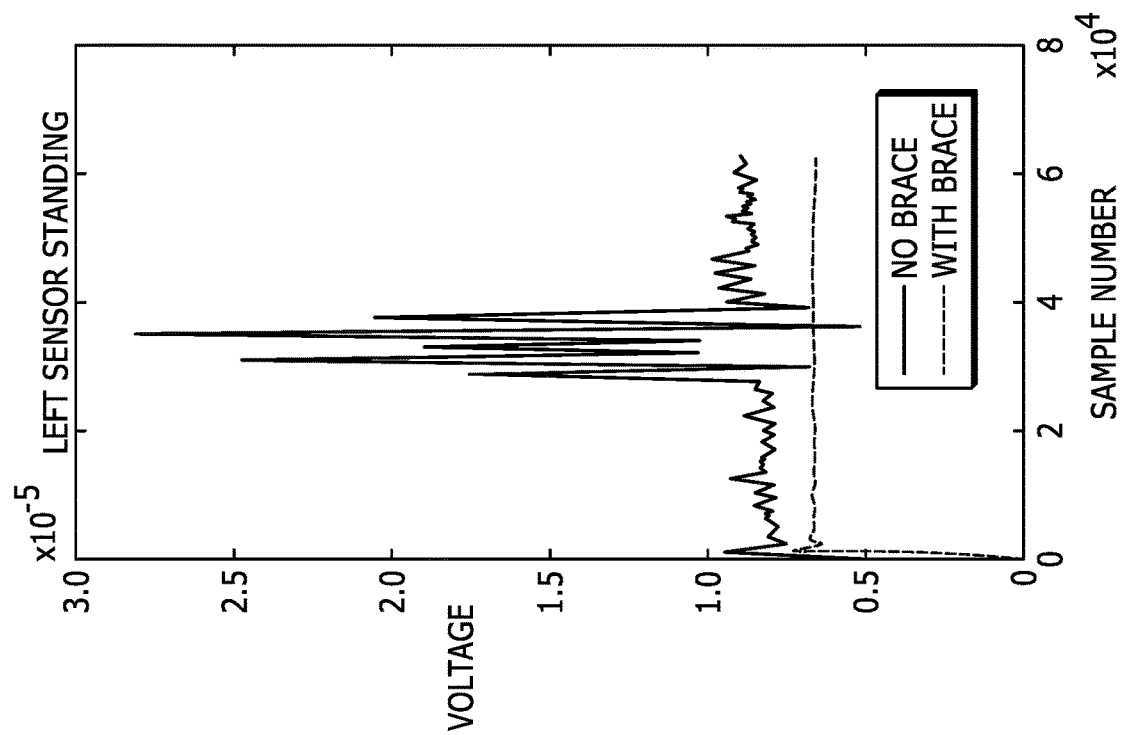
FIG. 12A is a graph comparing voltage readings from the first sensor while a user is standing with and without the orthosis device of FIG. 1.
Figure 13B:
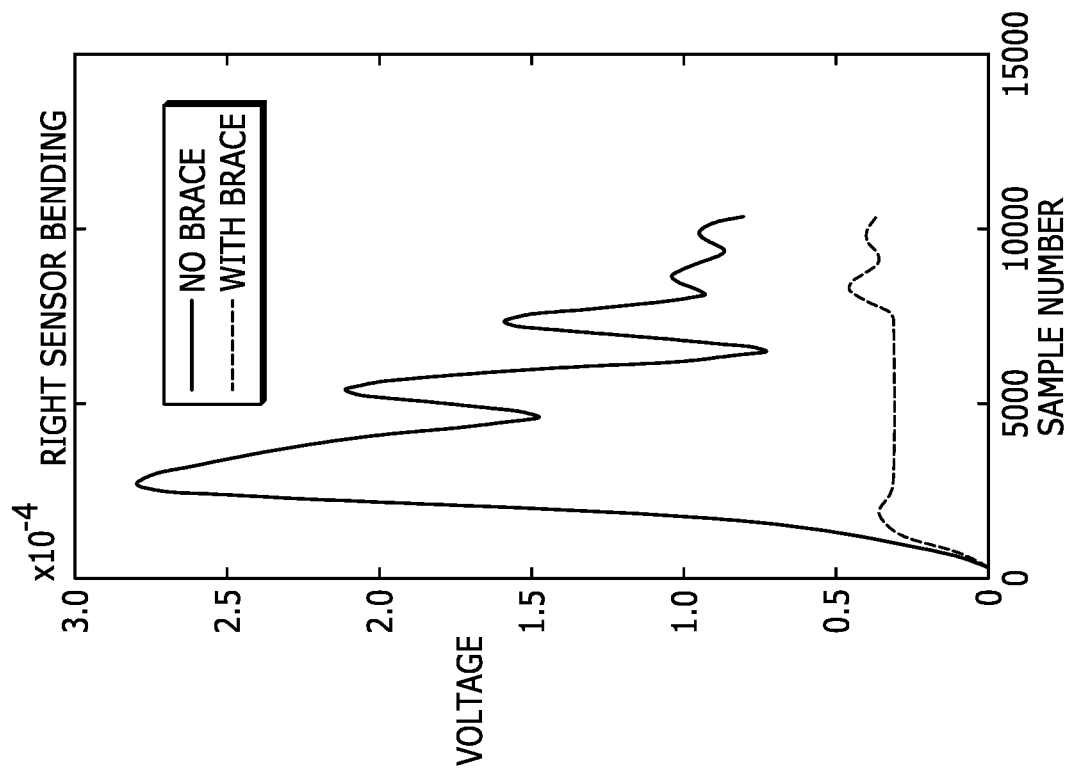
FIG. 13B is a graph comparing voltage readings from the second sensor while a user is bending over with and without the orthosis device of FIG. 1.
Figure 13A:
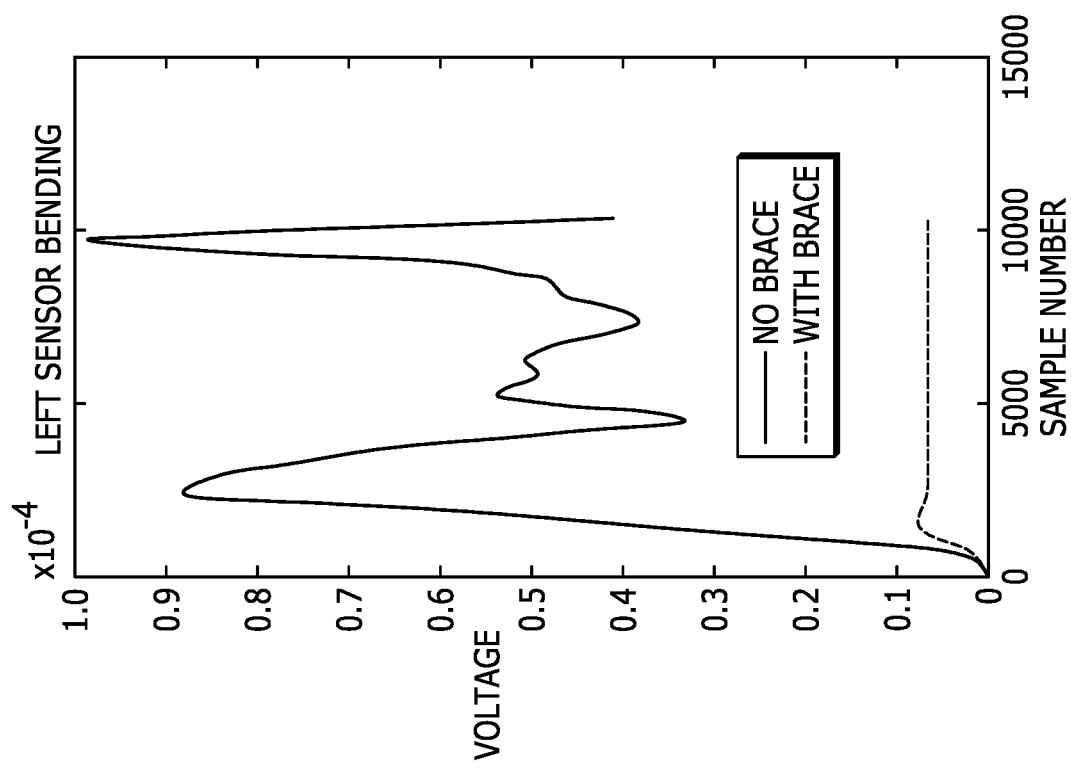
FIG. 13A is a graph comparing voltage readings from the first sensor while a user is bending over with and without the orthosis device of FIG. 1.

The orthosis device 110 utilizes the bladders 120a, 120b, 128, 132 to create the necessary forces to support a patient's spine. In some embodiments, a measured rectangular piece of thermoplastic polyurethane (TPU) material can be selected for the bladders 120a, 120b, 128, 132. In some embodiments, a rip-stop Nylon material with a single sided plastic layer can be used. In yet other embodiments, three of the edges of the rectangular piece can be heat sealed to create a pocket shape. A small hole can be formed in one of the pieces of TPU. A washer can be placed on a vented screw and forced through the small hole. The hole in the material may be smaller than the diameter of the vented screw to ensure a tight fit. In some embodiments, the protruding screw can be wrapped using pipe sealant tape and a nut can be screwed down over the screw. The nut and screw can be tightened to a suitable and secure tightness. In some embodiments, the remaining fourth edge of the rectangular piece can then be heat sealed. A fabric sleeve with an opening for the air bladder can be sewn while ensuring that the sewed sleeve is smaller than the air bladder. In some embodiments, the air bladder can be forced into the sleeve and a hole can be created in the sleeve through which the vented screw can be accessed. The sleeve can be sewn closed with the air bladder inside to create an encapsulated air bladder. In some embodiments of the orthotic device, there are eight total air bladders. In these embodiments, three sub-bladders 130a, 130b, 130c are placed in the rear fluid bladder 128 (see e.g., FIG. 9), three sub-bladders are placed in the front fluid bladder 132 (e.g., substantially identical to the rear fluid bladder 128), and the left and right bladders 120a, 120b (see e.g., FIG. 10) are placed on either side of the spinal column.

With reference to FIG. 7, the back orthosis 110 also includes a measuring device 190 (i.e., sensor or sensors) positioned on the back harness 114. In some embodiments, the measuring device 190 is an inertial measurement unit (IMU) that detects position and affects the stiffness of the back orthosis 110 accordingly. While wearing the back harness 114, a user may bend, or otherwise reposition his or her back and spine. The measuring device 190 records the position of the user's back relative to a vertical axis (e.g., the IMU measures a deflection angle between the user's back and the vertical).

In use, the orthosis device 10, 110 may be worn by a user while performing everyday activities. The user may actuate the power switch 48, and turn the orthosis device 10, 110 on. Electrical cables (not shown) may communicate electrical current from the battery 54 to the pneumatic device 40, 140 and/or the measuring device 190. As the user moves (e.g., bends forward), the measuring device 190 records the positions of the back, which are then communicated to the control device 36, 136 (e.g., via an electrical cable or wirelessly). The information from the measuring device 190 is received by the controller 66, which determines the magnitude of a force needed to support the torso. The controller 66 then communicates the information to the pumps 70 in the form of a pressure needed to be supplied to the bladders 120a, 120b, 128, 132. The pumps 70 increase or decrease the pressures in the various bladders 120a, 120b, 128, 132 in response to the signal received by the controller 166. The manifolds in the manifold housing 78 and the pressure sensors 74 work together to determine the pressure in each bladder 120a, 120b, 128, 132, and increase or decrease the fluid flow from the pumps 70 to each bladder 120a, 120b, 128, 132.

While the user's back is in a vertical position, the fluid bladders 120a, 120b, 128, 132 may be unpressurized (e.g., in a soft state). As the user bends, the pumps 70 supply air to the fluid bladders 120a, 120b, 128, 132, bringing them to a pressurized state (e.g., a rigid state). As the user returns to the upright position (i.e., the user's back returns to substantially vertical), the torque load caused by bending is absorbed by the bladders 120a, 120b, 128, 132, instead of the user's back. The fluid bladders 128, 132 assist in stabilizing a user's torso. The fluid bladders 120a, 120b limit flexion and/or extension of a user's back and spine.

In one experiment, sensors (not shown) were placed generally in the middle of a user's back to measure muscular responses to different activities (e.g., sitting (FIGS. 11A and 11B), standing (FIGS. 12A and 12B), and bending (FIGS. 13A and 13B)) in terms of voltage (i.e., an increase in voltage sensed corresponded to an increase in muscular activity). In this experiment, a sensor was placed on one side of the middle of the back (i.e., the left) and one sensor was placed on the other side of the back (i.e., the right). The test was performed without the orthosis device 10, 110 and then again with the orthosis device 10, 110. For a sitting test, the user sat in a chair without wearing the orthosis device 10, 110, and then while wearing the orthosis device 10, 110. For a standing test, the user stood from a sitting position without wearing the orthosis device 10, 110, and then stood while wearing the orthosis device 10, 110. For a bending test, the user bent to pick up an object without wearing the orthosis device 10, 110, and then bent again while wearing the orthosis device 10, 110. When the user wore the orthosis device 10, 110, the fluid bladders 20a, 20b, 28, 32, 120a, 120b, 128, 132 were pressurized. As shown in FIG. 11A-13B, both sensors measured lower voltage readings across all types of activities for the tests where the user wore the pressurized orthosis device 10, 110 than the tests where the user did not wear the orthosis device 10, 110 (i.e., the pressurized orthosis device 10, 110 decreased muscular activity in the back).

In some embodiments, the rear and front fluid bladders 128, 132 are designed in a "cascading" fashion, in that, a first or bottom sub-bladder 130c is larger than sub-bladders above it (e.g., a second or middle sub-bladder 130b and a third or top sub-bladder 130a). In some embodiments, the bottom sub-bladder 130c is 3×9 inches, the middle sub-bladder 130b is 2.5×9 inches, and the top sub-bladder 130a is 2×9 inches. In other embodiments, the dimensions of the top, middle, or bottom sub-bladders 130a, 130b, 130c may be different. The two bladders 120a, 120b disposed on the sides of the spinal column limit the flexion motion of the spine and may be designed in the same way as discussed above with multiple cascading sub-bladders. In some embodiments, these bladder dimensions are 3×13 inches. In other embodiments, these bladders 120a, 120b may have different dimensions. In some embodiments, the rear and front bladders 128, 132 are fixed in place by Velcro to the waist belt 118. This allows them to be replaced quickly if either bladder 128, 132 fails. This also allows a person (e.g., a physician) to readjust their position if they feel a user (e.g., a patient) would benefit from a lower or higher bladder actuation system. In some embodiments, the bladders 128, 132 that are placed in the front and back are secured to the waist belt 118 with a height $H_2$ of at least 9 inches. This will ensure that the bladders 128, 132 are achieving the correct forces to exert on the body. In some embodiments, a layer of padding is provided on top of one or more of the bladders 128, 132 to increase comfort for the patients. In some embodiments, the bladders 120a, 120b, 128, 132 are stitched to the back harness 114 and the waist belt 118 to create a secure attachment. In some embodiments, padding is added along the length of the bladders 120a, 120b, 128, 132 to increase patient comfort.

In some embodiments, the level of support (e.g., the pressure of the bladders 20a, 20b, 28, 32, 120a, 120b, 128, 132) and time when the orthosis device 10, 110 activates (e.g., position of user's back) can both be programmable. There may, for example, be a threshold position of the user which must be achieved before the pumps 70 are activated. There may also be different pressure levels in the bladders 120a, 120b, 128, 132 depending on the user's position. In some embodiments, the changeable parameters of the device can allow a doctor or fitting specialist to alter the support of the orthosis device 110 over the time span of a patient's recovery.

In some embodiments, the waist air bladders may utilize air pressure to gain stiffness by varying the psi inside the bladders. The orthosis device can become very stiff for motions such as bending and general movement. However, when the patient is sitting down, less stiffness is required and the air bladders can deflate completely to allow the patient to relax in a chair or bed without a bulky device on the waist. In some embodiments, one or more of the bladders 20a, 20b, 28, 32, 120a, 120b, 128, 132 can run parallel to the spine and limit flexion and extension motion of the spine. Limiting the bending of the back after surgery can promote spinal healing. In some embodiments, no rigid components are used as supports for the spinal column. The lack of rigid materials allows the device to be worn for longer periods of time without feeling pressure points from the hard pieces on the body.

In the event the pressure in any one of the bladders 20a, 20b, 128, 132, 120a, 120b, 128, 132 becomes too high, or the orthosis device 10, 110 malfunctions in any way, the user may actuate the emergency off switch 52. The emergency off switch 52 immediately cuts power from the controller 66, as well as the pumps 70, to prevent the bladders 20a, 20b, 128, 132, 120a, 120b, 128, 132 from further inflating. The emergency off switch 52 may also cause the bladders 20a, 20b, 128, 132, 120a, 120b, 128, 132 to depressurize and return to the unpressurized state.

It may be appreciated that the functions described above may be performed by multiple types of software applications, such as web applications or mobile device applications. These may be used as a way of programming or controlling the controller 66. If implemented in firmware and/or software, the functions described above may be stored as one or more instructions or code on a non-transitory computer-readable medium. Examples include non-transitory, computer-readable media encoded with a data structure and non-transitory, computer-readable media encoded with a computer program. Non-transitory, computer-readable media includes physical computer storage media. A physical storage medium may be any available medium that can be accessed by a computer. By way of example, and not limitation, such non-transitory computer-readable media can comprise RAM, ROM, EEPROM, CD-ROM or other optical disk storage, magnetic disk storage or other magnetic storage devices, or any other physical medium that can be used to store desired program code in the form of instructions or data structures and that can be accessed by a computer. Disk and disc includes compact discs (CD), laser discs, optical discs, digital versatile discs (DVD), floppy disks and Blu-ray discs. Generally, disks reproduce data magnetically, and discs reproduce data optically. Combinations of the above are also included within the scope of non-transitory computer-readable media. Moreover, the functions described above may be achieved through dedicated devices rather than software, such as a hardware circuit comprising custom VLSI circuits or gate arrays, off-the-shelf semiconductors such as logic chips, transistors, or other discrete components, all of which are non-transitory. Additional examples include programmable hardware devices such as field programmable gate arrays, programmable array logic, programmable logic devices or the like, all of which are non-transitory. Still further examples include application specific integrated circuits (ASIC) or very large scale integrated (VLSI) circuits. In fact, any number of suitable structures capable of executing logical operations may be used according to the described embodiments.

Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the disclosed methods, devices, and systems are not intended to be limited to the particular forms disclosed. Rather, they include all modifications and alternatives falling within the scope of the claims, and embodiments other than those shown may include some or all of the features of the depicted embodiment. For example, components may be combined as a unitary structure and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments Although the invention has been described in detail with reference to certain preferred embodiments, variations and modifications exist within the scope and spirit of one or more independent aspects of the invention as described.

What is claimed is:

1. A soft robotic spinal orthosis apparatus, the apparatus comprising:
    a control system having at least one processor;
    a plurality of adjustable pressure fluid bladders configured to provide at least one variable supporting force to a torso of a user;
    a plurality of supports configured to secure the plurality of fluid bladders to the torso;
    at least one sensor configured to detect a position of the torso; and
    at least one pressure device configured to increase and decrease a fluid pressure in the plurality of fluid bladders;
    wherein the plurality of fluid bladders includes at least one fluid bladder configured to support a front of a waist of the user and at least one fluid bladder configured to support a back of the waist, wherein at least one of the fluid bladders is arranged in a cascading configuration along a height of the waist, and includes a first, upper sub-bladder, a second sub-bladder below the first sub-bladder, and a third, lower sub-bladder below the second sub-bladder, wherein the third sub-bladder is larger than the second sub-bladder and the second sub-bladder is larger than the first sub-bladder.

2. The apparatus of claim 1, wherein the control system is configured to:
    receive a torso position from the at least one sensor;
    determine a magnitude of the at least one variable supporting force sufficient to support the torso based on the torso position;
    enable the at least one pressure device to modify a pressure of the plurality of fluid bladders to supply the at least one variable supporting force to the torso at the determined magnitude.

3. The apparatus of claim 2, wherein the control system is programmable and configured to control one or more variable supporting force magnitudes and one or more variable supporting force application time intervals.

4. The apparatus of claim 1, wherein the plurality of fluid bladders includes fluid bladders extending along a spine of the torso configured to support the spine.

5. The apparatus of claim 4, wherein the fluid bladders configured to support the waist are configured to stabilize the torso and the fluid bladders extending along the spine are configured to limit one or more of flexion and extension motions of the spine.

6. The apparatus of claim 1, wherein the at least one sensor is an inertial measuring unit (IMU).

7. The apparatus of claim 1, wherein the at least one pressure device includes:
    at least one pump configured to provide fluid pressure;
    at least one manifold having at least one valve configured to receive the fluid pressure from the at least one pump; and
    at least one pressure sensor configured to determine a fluid pressure inside the plurality of fluid bladders and control an inflow and outflow of fluid pressure to the plurality of fluid bladders.

* * * * *